United States Patent [19]

Takaishi et al.

[11] 3,976,706

[45] Aug. 24, 1976

[54] PROCESS FOR THE PREPARATION OF TRICYCLE [5.3.1.0$^{3,8}$]UNDECANE

[75] Inventors: Naotake Takaishi; Yoshiaki Inamoto, both of Wakayama; Kiyoshi Tsuchihashi, Kainan, all of Japan

[73] Assignee: Kao Soap Co., Ltd., Tokyo, Japan

[22] Filed: July 2, 1974

[21] Appl. No.: 485,067

[30] Foreign Application Priority Data

July 10, 1973 Japan.............................. 48-77622

[52] U.S. Cl..................... 260/666 PY; 260/666 M
[51] Int. Cl.$^2$..................... C07C 5/24; C07G 13/54
[58] Field of Search.................. 260/666 PY, 666 M

[56] References Cited
UNITED STATES PATENTS 3,356,751  12/1967  Schneider...................... 260/666 M

OTHER PUBLICATIONS

A. Krantz et al., *Chem. Comm.* 1287–1288, 1971.
A. Krantz et al., *J. Am. Chem. Soc.* 95, 5662–5672, 1973.
K. M. Majerski et al., *Tetrahedron Letters*, No. 49, 4915–4918, 1973.
Malrine Farcasin et al., *Chemistry Letters*, 1189–1182, 1973.
Derek J. Cash et al. Tetrahedron Letters, No. 52, pp. 6445–6451, 1966.

*Primary Examiner*—Veronica O'Keefe
*Attorney, Agent, or Firm*—Woodhams, Blanchard and Flynn

[57] ABSTRACT

A process for the preparation of tricyclo[5.3.1.0$^{3,8}$]-undecane in which tricyclo[5.2.2.0$^{2,6}$]undecane is isomerized in the presence of an acid catalyst.

4 Claims, No Drawings

PROCESS FOR THE PREPARATION OF TRICYCLO [5.3.1.0$^{3,8}$]UNDECANE

BACKGROUND OF THE INVENTION
1. FIELD OF THE INVENTION

This invention relates to a process for the preparation of tricyclo[5.3.1.0$^{3,8}$]undecane (II) by the acid catalyzed isomerization of tricyclo[5.2.2.0$^{2,6}$]undecane (I) according to the following reaction scheme (1):

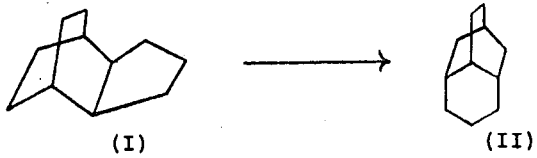

2. DESCRIPTION OF THE PRIOR ART

So far as we are aware, there are known the three tricycloundecane compounds: tetramethylenenorbornane (III) [Alder, et al., Ann., 627, 47 (1959)], homoadamantane (IV) [Stetter, et al., Ber., 96, 550 (1963)], tricyclo[5.3.1.0$^{2,6}$]undecane (V) [Petrov, et al., Neftekhimiya, 11, 163 (1971)].

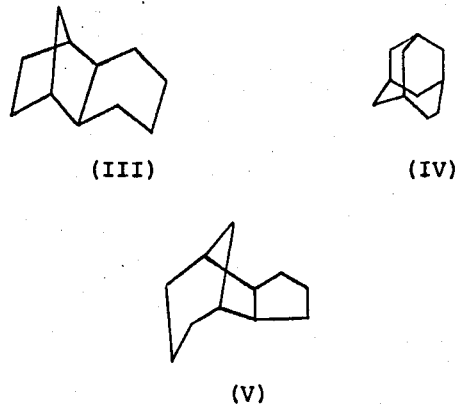

In addition to these, we have recently proposed tricyclo[5.2.2.0$^{2,6}$]undecane (I) which is used as the starting substance in this invention. This substance (I) was synthesized for the first time by Applicants (see Japan Patent Application No. 106,514/72, corresponding to U.S. Patent Application Ser. No. 404,195, filed October 9, 1973, the entire contents of which are incorporated herein by reference).

SUMMARY OF THE INVENTION

It has now been found that tricyclo[5.3.1.0$^{3,8}$]undecane (II), a novel tricycloundecane compound, can be synthesized from tricyclo[5.2.2.0$^{2,6}$]undecane by the process of this invention.

We have discovered that under certain reaction conditions the isomerization of tricyclo[5.2.2.0$^{2,6}$]undecane, which would otherwise lead to the final formation of 1- and 2-methyladamantane, can be interrupted at a stage in which an intermediate, the novel compound tricyclo[5.3.1.0$^{3,8}$]undecane (II), is the main constituent of the reaction mixture. More specifically, in accordance with this invention, there is provided a process in which tricyclo[5.3.1.0$^{3,8}$]undecane (II) can be synthesized simply by isomerizing tricyclo[5.2.2.0$^{2,6}$]undecane (I) in the presence of an acid catalyst under controlled reaction conditions.

Various research investigations have heretofore been made on the isomerization of tricycloundecanes to produce 1-methyladamantane (Schleyer, et al., *Tetrahedron Letters*, 305 (1961); Schneider, et al., U.S. Pat. No. 3,356,751; McKervey, et al., *Tetrahedron Letters*, 27, 4317 (1971); Petrov, et al., *Neftekhimiya*, 11, 163 (1971)). However, there is known no instance in which any reaction intermediates are isolated. As a result of our investigations on the mechanism of the acid-catalyzed isomerization of tricyclo[5.2.2.0$^{2,6}$]undecane (I), we found that this tricyclo[5.2.2.0$^{2,6}$]undecane (I) can be isomerized to 1-methyladamantane in a substantially quantitative yield (see Japan Patent Application No. 106374/72, corresponding to U.S. Patent Application Serial No. 404,195). It has been found that this isomerization reaction is a series of consecutive reactions in which tricyclo[5.2.2.0$^{2,6}$]undecane (I) substantially disappears in the course of the reaction to form a mixture of several reaction intermediates including tricyclo[5.3.1.0$^{3,8}$]undecane (II). These intermediates are converted during the further course of the reaction to 1- and 2-methyladamantanes. More specifically, it has been found that when the acid-catalyzed isomerization reaction of tricyclo[5.2.2.0$^{2,6}$]undecane (I) is interrupted at an appropriate stage or when the above isomerization reaction is conducted under milder conditions than those adopted for complete isomerization to form 1-methyladamantane, a reaction intermediate mixture consisting substantially of tricyclo[5.3.1.0$^{3,8}$]undecane (II) can be obtained, and that the separation of the mixture by appropriate means such as distillation or chromatography, gives tricyclo[5.3.1.0.$^{3,8}$]undecane (II) in a yield of 40 to 75 percent.

Thus, the process of this invention is characterized by the features that the starting tricyclo[5.2.2.0$^{2,6}$]undecane (I) is isomerized under controlled mild reaction conditions. In contrast, if tricyclo[5.2.2.0$^{2,6}$]undecane (I) is isomerized under strong conditions, the final product, 1-methyladamantane, is directly formed in a very short time and is present in a mixture of tricyclic undecanes including the intermediate (II) that are difficult to isolate from each other.

The term "strong reaction conditions" in this specification means that the reaction is carried out in the absence of a solvent at a temperature higher than 50°C. by employing as a catalyst a strong Lewis acid such as aluminum halides and antimony pentahalides in an amount of at least 50 mole percent based on the starting substance (I). In contrast, the term "controlled mild conditions" which characterize this invention giving intermediate products including a large amount of the desired product (II) of this invention means that the reaction is carried out in the presence of a solvent, at a temperature below 60°C., and by employing as a catalyst a Bronsted acid or a Lewis acid in an amount of up to 20 mole percent of (I), and that the reaction is conducted while following the reaction by examining the amount formed of the product (II) by, for example, gas chromatography, the reaction being stopped at the point when the concentration of the desired product (II) reaches the highest level.

As the catalyst suitable for attaining these said mild reaction conditions, various acid catalysts are effectively employed. Among them, there are preferably employed Bronsted acids such as sulfuric acid, fluorosulfonic acid, chlorosulfonic acid, methanesulfonic acid, ethanesulfonic acid, trifluoromethanesulfonic acid, benzenesulfonic acid, and p-toluenesulfonic acid, and Lewis acids such as aluminum halides, preferably aluminum chloride and aluminum bromide, zinc halides, preferably zinc chloride and zinc bromide, boron halides, preferably boron trifluoride, and antimony halides, preferably antimony pentafluoride, in an amount up to 20 mole percent of (I). In the case of a Bronsted acid such as various sulfonic acids, the amount of the catalyst used is not particularly critical, and in order to complete the reaction in a short period of time it is permissible to use the catalyst in an equimolar amount or even in excess, based on the staring substance (I), i.e. from 0.1 to about 50 moles of Bronsted acid permole of (I). In contrast, in the case of a Lewis acid such as aluminum halides, the desired product can be effectively obtained if the catalyst is used in an amount of 0.01 to 0.2 mole, preferably 0.03 to 0.1 mole, per mole of the starting tricyclo[5.2.2.0⁶]-undecane (I). If the catalyst is used in an amount exceeding the above range, the object of this invention cannot be attained because isomerization of the desired product (II) to 1-methyladamantane is also caused to proceed and the reaction product is difficult to separate.

The solvent used is not particularly critical, and any of the solvents unreactive to the catalyst, such as aromatic hydrocarbons, aliphatic hydrocarbons, halogenated hydrocarbons and ethers can be used in the invention. We can thus use any solvent inert to the reaction.

As the solvent, it is preferred to use halogenated lower hydrocarbons, preferably chlorinated or brominated hydrocarbons containing 1 to 6 carbon atoms such as methylene chloride, methylene bromide, chloroform, 1,2-dichloroethane, 1,2-dibromoethane, 1,2-dichloropropane, 1,3-dichloropropane, 1,3-dichlorobutane, 2-methyl-1,4-dichlorobutane, chlorocyclohexane and the like. The amount of solvent employed is from 0.1 to 500 times the weight of the starting material I.

The reaction proceeds at a temperature ranging from −30 to 100°C., but it is preferred that the reaction is carried out at a temperature below 60°C, for example in the range of −10 to 50°C.

This invention will now be further described by reference to the following illustrative Examples. Because the product of this invention, tricyclo[5.3.1.0³,⁸]undecane (II), is a novel compound, its structure determination is also shown in Examples.

EXAMPLE 1

A solution of 15 g (0.1 mole) of tricyclo[5.2.2.0²,⁶]-undecane (I) in 100 ml of methylene chloride was agitated at 0°C. Then, 1.3 (0.01 mole) of anhydrous aluminum chloride was added to the solution, and the mixture was heated and refluxed under agitation for 1 hour. The reaction mixture was allowed to cool and then poured over 100 ml of ice water. The organic layer was separated and the aqueous layer was extracted with methylene chloride. The methylene chloride extract was combined with the organic layer, and the mixture was washed with a saturated aqueous solution of sodium hydrogencarbonate and then with water, and then dried over anhydrous sodium sulfate. Methylene chloride was distilled off, and the residue was subjected to fractionation. The highest boiling point fraction (boiling at 111° to 112°C. under 36 mmHg) was separated, whereby 6.3 g (yield: 42%) of tricyclo[5.3.1.0³,⁸]-undecane was obtained.

Melting Point:
62°–63°C. (sealed tube)
Elemental Analysis:
Found: C, 87.8; H, 12.2%.
Calculated for $C_{11}H_{18}$: C, 87.92; H, 12.08%.
IR Spectrum (cm⁻¹):
2925, 2890, 2870, 2850, 1480, 1465, 1450, 1340, 975, 895, 845
Mass Spectrum (m/e) (relative intensity):
150 (M⁺, 100), 122 (39), 121 (39), 109 (12), 108 (16), 107 (19), 93 (27), 81 (27), 80 (46), 79 (40), 67 (35), 55 (18), 41 (40)
¹H NMR Spectrum (CDCl₃ solvent): δ1.0 – 2.0 ppm, complex multiplet
¹³C NMR Spectrum (CDCl₃ solvent, 15.1 MHz, TMS at 0 ppm) (ppm):
15.2, 24.8, 26.3, 27.1, 30.9, 31.9, 32.3, 33.1.

In view of the fact that the melting point is relatively high (62°–63°C.) through the product is a saturated hydrocarbon having 11 carbon atoms and both IR and ¹H NMR spectra are simple, it is considered from the data that the product has a highly symmetric structure. Further, the fact that in the mass spectrum the parent peak is the base peak, is evidence that the product is a cage molecule. Eight kinds of carbon atoms are observed in the ¹³C NMR spectrum, and therefore, the product can be considered to be tricyclo[5.3.1.0³,⁸]undecane (II) or tricyclo[4.4.1.0²,⁸]undecane of the following formula (VI):

(VI)

However, the compound (VI) includes a 7-membered ring and has a great distortion. Therefore, it cannot be considered to be an intermediate that can be isolated in a stable condition.

In view of the foregoing, it is concluded that the isolated product is tricyclo[5.3.1.0³,⁸]undecane (II).

EXAMPLE 2

A solution of 15 g (0.1 mole) of tricyclo[5.2.2.0²,⁶]-undecane (I) in 100 ml of methylene chloride was agitated at 0°C, and 15 g (0.1 mole) of trifluoromethanesulfonic acid was added to the solution. Then, the mixture was heated and refluxed for 6 hours under agitation. The reaction mixture was allowed to cool and poured over 100 ml of ice water. The organic layer was separated and the aqueous layer was extracted with methylene chloride. The methylene chloride extract was combined with the organic layer, and the mixture was washed with a saturated aqueous solution of sodium hydrogencarbonate and then with water, and then dried over anhydrous sodium sulfate. Methylene chloride was distilled off, and the residue was subjected to fractionation and a fraction boiling at 110° – 115°C. under 36 mmHg was collected, whereby 6.6 g (yield: 44 wt.%) of tricyclo[5.3.1.0³,⁸]undecane (II) was obtained. All of the IR, NMR and MS spectra of the thus obtained compound were in agreement with those of the product (II) obtained in Example 1.

EXAMPLE 3

A mixture of 7.5 g (0.05 mole) of tricyclo[5.2.2.0$^{2,6}$]-undecane (I) and 7.5 g of 96 percent concentrated sulfuric acid was heated at 40°C. under agitation for 5 hours. The reaction mixture was allowed to cool and then poured over 100 ml of ice water. The organic layer was separated and the aqueous layer was extracted with methylene chloride. The methylene chloride extract was combined with the organic layer, and the mixture was washed with a saturated aqueous solution of sodium hydrogencarbonate and then with water, and then dried over anhydrous sodium sulfate.

When the dried mixture was subjected to gas chromatography (column: Chromosorb AW containing 30% SE-30, column temperature: 110°C, carrier gas: helium), it was found that only 15 wt.% of unreacted tricyclo[5.2.2.0$^{2,6}$]undecane (I) and 85 wt.% of tricyclo[5.3.1.0$^{3,8}$]undecane (II) were detected, but no other reaction intermediate was detected.

Methylene chloride was distilled off, and the residue was subjected to fractionation. A fraction boiling at 108° – 115°C. under 36 mmHg was collected, whereby 5.6 g (the yield being 75%) of tricyclo[5.3.1.0$^{3,8}$]undecane (II) was obtained. All of the IR, NMR and MS spectra of the so-obtained product were in agreement with those of the product (II) obtained in Example 1.

Tricyclo[5.3.1.0$^{3,8}$]undecane can be isomerized to form 1-methyladamantane, a known useful compound, by the process described in Japanese patent application 77623/73, filed July 10, 1973, and the corresponding U.S. patent application Ser. No. 485,069, filed July 2, 1974, being filed concurrently herewith (Attorney's Reference Furuya Case 359), the entire contents of which are incorporated herein by reference. The following examples describe the preparation of 1-methyladamantane from tricyclo[5.3.1.0$^{3,8}$]undecane.

EXAMPLE 4

A solution of 15 g (0.1 mole) of tricyclo[5.3.1.0$^{3,8}$]-undecane (II) in 100 ml of methylene chloride was agitated at 0°C, and 2.0 g (0.015 mole) of anhydrous aluminum chloride was added to the solution. The mixture was heated and refluxed under agitation for 6 hours, and the resulting reaction mixture was allowed to cool and poured over 100 ml of ice water. The organic layer was separated, and the water layer was extracted with methylene chloride. The methylene chloride extract was combined with the organic layer, and the mixture was washed with a saturated aqueous solution of sodium hydrogencarbonate and then with water, and then dried over anhydrous sodium sulfate. Methylene chloride was distilled off and the residue was sublimed to obtain 13.7 g (yield: 91 wt.%) of 1-methyladamantane. All of the IR, NMR and MS spectra were in agreement with those of the authentic sample synthesized from tetramethylenenorbornane according to the method of Schleyer, et al. [Tetrahedron Letters, 305 (1961)].

EXAMPLE 5

A mixture of 7.5 g (0.05 mole) of tricyclo[5.3.1.0$^{3,8}$]-undecane (II) and 76 g (0.5 mole) of trifluoromethanesulfonic acid was heated at 80°C. for 30 hours under agitation. The reaction mixture was allowed to cool and then poured over 200 ml of ice water. The organic layer was separated and the water layer was extracted with methylene chloride. The methylene chloride extract was combined with the organic layer, and the mixture was washed with a saturated aqueous solution of sodium hydrogencarbonate and then with water, and dried over anhydrous sodium sulfate. Methylene chloride was distilled off and the residue was sublimed to obtain 6.8 g (yield: 90 wt.%) of 1-methyladamantane (II). All of the IR, NMR and MS spectra of the product were in agreement with those of the authentic sample.

The embodiments of this invention in which an exclusive property or privilege is claimed are defined as follows:

1. A process for preparing tricyclo[5.3.1.0$^{3,8}$]undecane which comprises isomerizing tricyclo[5.2.2.0$^{2,6}$]undecane in an inert solvent, at a temperature in the range of −30° to 100°C, in the presence of an acid catalyst selected from the group consisting of (1) a Bronsted acid and (2) a Lewis acid in an amount of 0.01 to 0.2 mole per mole of starting tricyclo[5.2.2.0$^{2,6}$]undecane, terminating the isomerization reaction when the content of tricyclo[5.3.1.0$^{3,8}$]undecane in the reaction mixture is at least about 40 wt.%, excluding the solvent and acid catalyst, and recovering tricyclo[5.3.1.0$^{3,8}$]undecane from the reaction mixture.

2. The process according to claim 1 wherein the temperature of the isomerization reaction is in the range of −10° to 50°C.

3. The process according to claim 2 wherein the acid catalyst is a member of the group consisting of fluorosulfonic acid, p-toluenesulfonic acid, methanesulfonic acid, ethanesulfonic acid, sulfuric acid and trifluoromethanesulfonic acid.

4. The process according to claim 2 wherein the acid catalyst is 0.03 to 0.1 mole of a member of the group consisting of an aluminum halide and antimony pentahalide per mole of starting tricyclo[5.2.2.0$^{2,6}$]undecane.

* * * * *